United States Patent
Placik (10) Patent No.: US 11,273,232 B2
(45) Date of Patent: Mar. 15, 2022

(54) ISOLATION SYSTEM FOR A HANDHELD ELECTRONIC DEVICE THAT ENABLES USE WITHIN A CLEAN ENVIRONMENT

(71) Applicant: Otto J. Placik, Arlington Heights, IL (US)

(72) Inventor: Otto J. Placik, Arlington Heights, IL (US)

( * ) Notice: Subject to any disclaimer, the term of this patent is extended or adjusted under 35 U.S.C. 154(b) by 77 days.

(21) Appl. No.: 16/751,123

(22) Filed: Jan. 23, 2020

(65) Prior Publication Data
US 2021/0228756 A1 Jul. 29, 2021

(51) Int. Cl.
*A61L 2/26* (2006.01)
*A45C 11/00* (2006.01)
*B65B 5/04* (2006.01)
*B65B 7/08* (2006.01)

(52) U.S. Cl.
CPC ............. *A61L 2/26* (2013.01); *A45C 11/00* (2013.01); *B65B 5/045* (2013.01); *B65B 7/08* (2013.01); *A45C 2011/002* (2013.01); *A61L 2202/181* (2013.01)

(58) Field of Classification Search
CPC ...... A61L 2/26; A61L 2202/181; A45C 11/00; A45C 2011/002; B65B 7/2864; B65B 5/04; B65B 7/08
USPC .......... 206/320; 383/205, 11, 6, 13; 150/165
See application file for complete search history.

(56) References Cited

U.S. PATENT DOCUMENTS

| | | | | |
|---|---|---|---|---|
| 5,499,713 A | * | 3/1996 | Hutter | H01H 9/0242 206/320 |
| 5,957,831 A | * | 9/1999 | Adair | A61B 1/00142 600/101 |
| 8,475,365 B2 | * | 7/2013 | Modin | A61B 46/10 600/122 |
| 8,550,713 B2 | | 10/2013 | Schwarz | |
| 8,672,127 B1 | * | 3/2014 | Clover | H01H 9/0242 206/320 |
| 9,642,429 B2 | | 5/2017 | Zondervan | |
| 2004/0154941 A1 | * | 8/2004 | Montler | H01H 9/0242 206/320 |
| 2005/0092636 A1 | * | 5/2005 | Su-Syin | A61L 2/26 206/363 |
| 2006/0196792 A1 | * | 9/2006 | Barth | B65D 31/02 206/320 |
| 2012/0008880 A1 | * | 1/2012 | Toth | A45C 13/008 383/42 |

(Continued)

FOREIGN PATENT DOCUMENTS

WO    WO-2015195626 A1 * 12/2015 .............. A61L 2/28

*Primary Examiner* — Rafael A Ortiz
(74) *Attorney, Agent, or Firm* — LaMorte & Associates P.C.

(57) ABSTRACT

An isolation bag assembly that holds an electronic device so it can be introduced into a clean environment. A sterilized bag structure is provided. The bag structure also has a front panel, a rear panel, a closed bottom, an open top, a first side edge, and a second side edge. When an electronic device is placed inside the bag structure, the device is positioned in a clear area. Adhesive tabs are affixed to the bag structure surrounding the clear area. The first edge and the open top of the bag structure are folded towards the clear area. The folds are held in place by the adhesive tabs. The folds make the bag structure conform to the shape of the electronic device and remain taut.

9 Claims, 7 Drawing Sheets

(56) References Cited

U.S. PATENT DOCUMENTS

| | | | |
|---|---|---|---|
| 2012/0174373 A1* | 7/2012 | Whitney | A45C 11/38 29/428 |
| 2012/0202000 A1* | 8/2012 | Bricker | A61L 2/26 428/99 |
| 2013/0001283 A1* | 1/2013 | Friderich | B65D 65/06 229/87.01 |
| 2013/0064478 A1 | 3/2013 | Sold et al. | |
| 2013/0081355 A1* | 4/2013 | Gaynor | A61L 2/26 53/167 |
| 2014/0270583 A1* | 9/2014 | Anderson | B65D 33/001 383/37 |
| 2015/0311008 A1* | 10/2015 | Nadalet | H01H 9/0242 206/320 |

* cited by examiner

ISOLATION SYSTEM FOR A HANDHELD ELECTRONIC DEVICE THAT ENABLES USE WITHIN A CLEAN ENVIRONMENT

BACKGROUND OF THE INVENTION

1. Field Of The Invention

In general, the present invention relates to the structure of isolation bags that are used to isolate objects so that they can be introduced into a clean environment without having to be decontaminated. More particularly, the present invention relates to isolation bags that are designed to hold electronic devices, such as smartphones, in a clean environment.

2. Prior Art Description

Many procedures, such as any invasive surgical procedure, are required to be performed in a clean environment. That is, the environment must be substantially free of particulate and biological contaminants that may inadvertently enter the body during the procedure and cause harm. As a result, great care is taken by hospitals, clinics, physicians and support staff to maintain a clean medical environment. This is especially true during an invasive medical procedure, where only decontaminated and gloved personnel are permitted to approach the patient.

Medical professionals, like much of the population, are becoming more reliant on smart phones to perform various tasks. Smartphones are used for taking pictures, viewing pictures, recording notes and of course communicating with others. Many of these functions are useful to a medical professional during an operation. For example, a medical professional may want to record images and/or spoken notes during a procedure. The problem is that smartphones, tablets and other such electronic devices cannot be effectively decontaminated without harming the electronic device. This is because most decontamination procedures require autoclaving with exposure to high temperatures, high pressures, and or antiseptic agents.

In an attempt to bring handheld electronic devices into clean environments, the traditional procedure involves encapsulating the electronic device in a sterile container and then attempting to operate the handheld electronic device within the confines of the container. For example, in U.S. Pat. No. 9,642,429 to Zondervan, a container is provided for a smartphone that enables the smartphone to be operated without touching the smartphone. The problem with such products is that they must be customized for each make and model of smartphone. This makes the container expensive to produce, which is highly undesirable for a disposable prophylactic product.

One of the least expensive and most effective ways to isolate a smartphone or other such electronic device, is to place the device in a clear plastic bag that has been sterilized. This is the most common procedure that is used today. Often the bag used is a common sandwich bag. However, specialty bags have been developed for this purpose. The specialty bags are exemplified by U.S. Patent Application Publication No. 2014/0270583 to Andersen, and U.S. Patent Application Publication No. 2012/0174373 to Whitney. The problem with the use of plastic bags is that the bags typically come in one size. As such, the plastic bags are made large to accommodate smartphones and other electronic devices of various sizes. The result is that the bag is often too large and a smart-phone or other device lays loose in the bottom of the bag. This makes the device very hard to grasp because the gloved user must grasp the bag in such a manner that captures the device within the bag. This is difficult to do, especially if the user's gloves are wet and slick. Likewise, once the bag is grasped, it is difficult to operate the electronic device within the bag. This is especially true the device has a touch screen that must be swiped. Furthermore, since the bag is loose around the electronic device, the bag becomes gathered when grasped. This creates numerous folds and wrinkles in the bag around the electronic device. The folds and wrinkles distort light received by the electronic device and greatly degrades the quality of any photos or videos taken using the bagged electronic device. Likewise, the folds and wrinkles make images on the electronic device difficult to clearly view. Additionally, the loose bag makes noise when grasped and manipulated. This makes it difficult to record spoken words and other sounds using the electronic device.

A need therefore exists for an improved bag assembly that can be used to isolate a smartphone or similar electronic device so that the device can be brought into a clean environment. A need further exists for an improved bag assembly that can be adjusted in size to match the dimensions of the electronic device, while remaining taut and unwrinkled around the functional surfaces of the electronic device. These needs are met by the present invention as described and claimed below.

SUMMARY OF THE INVENTION

The present invention is an isolation bag assembly that holds an electronic device, such as a smartphone, so that the electronic device can be introduced into a clean environment. A sterilized bag structure is provided that is made from a flexible clear plastic. The bag structure has a first length and a first width. The bag structure also has a front panel, a rear panel, a closed bottom, an open top, a first side edge, and a second side edge. To form the bag structure, the first panel and the second panel are joined along the closed bottom, the first side edge and the second side edge.

When the electronic device is placed inside the bag structure, the device is positioned in a clear area against the bottom and rear edge of the bag structure. A plurality of adhesive tabs are affixed to the first panel of the bag structure surrounding the clear area that holds the electronic device.

The first edge of the bag structure is folded towards the clear area that holds the electronic device. The fold is held in place by one or more adhesive tabs that extend across the fold between the front panel and the rear panel. Furthermore, the open top is closed and folded toward the clear area that holds the electronic device. This second fold is held in place by a secondary adhesive tab that extends across the fold between the first panel and the second panel. By folding the bag structure to the clear area of the electronic device, the bag structure is made to conform to the shape of the electronic device and is held taut over the control surfaces of the electronic device. The result is an assembly that is sterile but is easy to hold operate.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

Although the present invention isolation bag assembly can be embodied in many ways, only one exemplary embodiment is illustrated. The exemplary embodiment is being shown for the purposes of explanation and description. The exemplary embodiment is selected in order to set forth one of the best modes contemplated for the invention. The illustrated embodiment, however, is merely exemplary and should not be considered a limitation when interpreting the scope of the appended claims.

Figure 1:
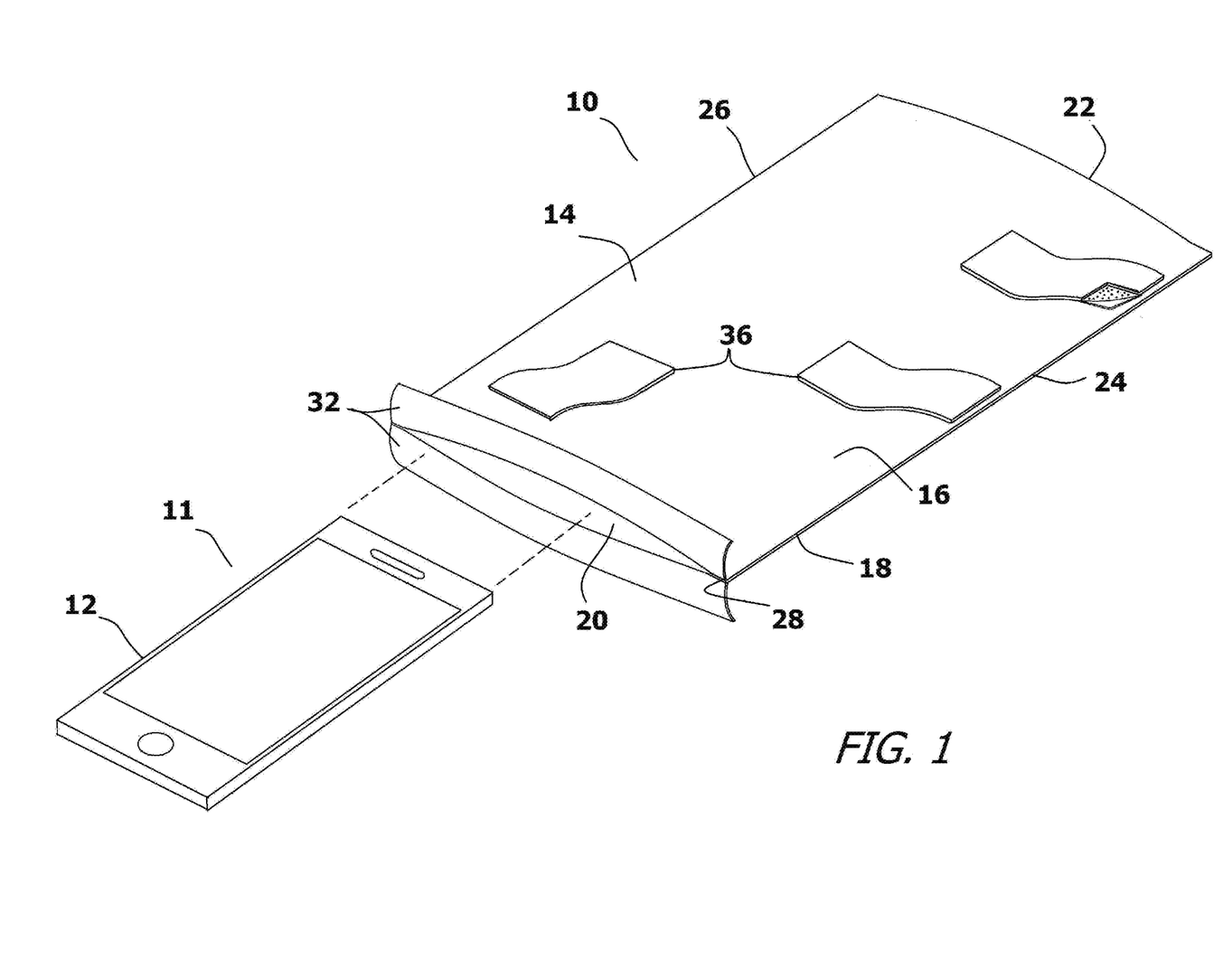
FIG. 1 is a perspective view of an exemplary embodiment of an isolation bag assembly shown in conjunction with a handheld electronic device.
Figure 2:
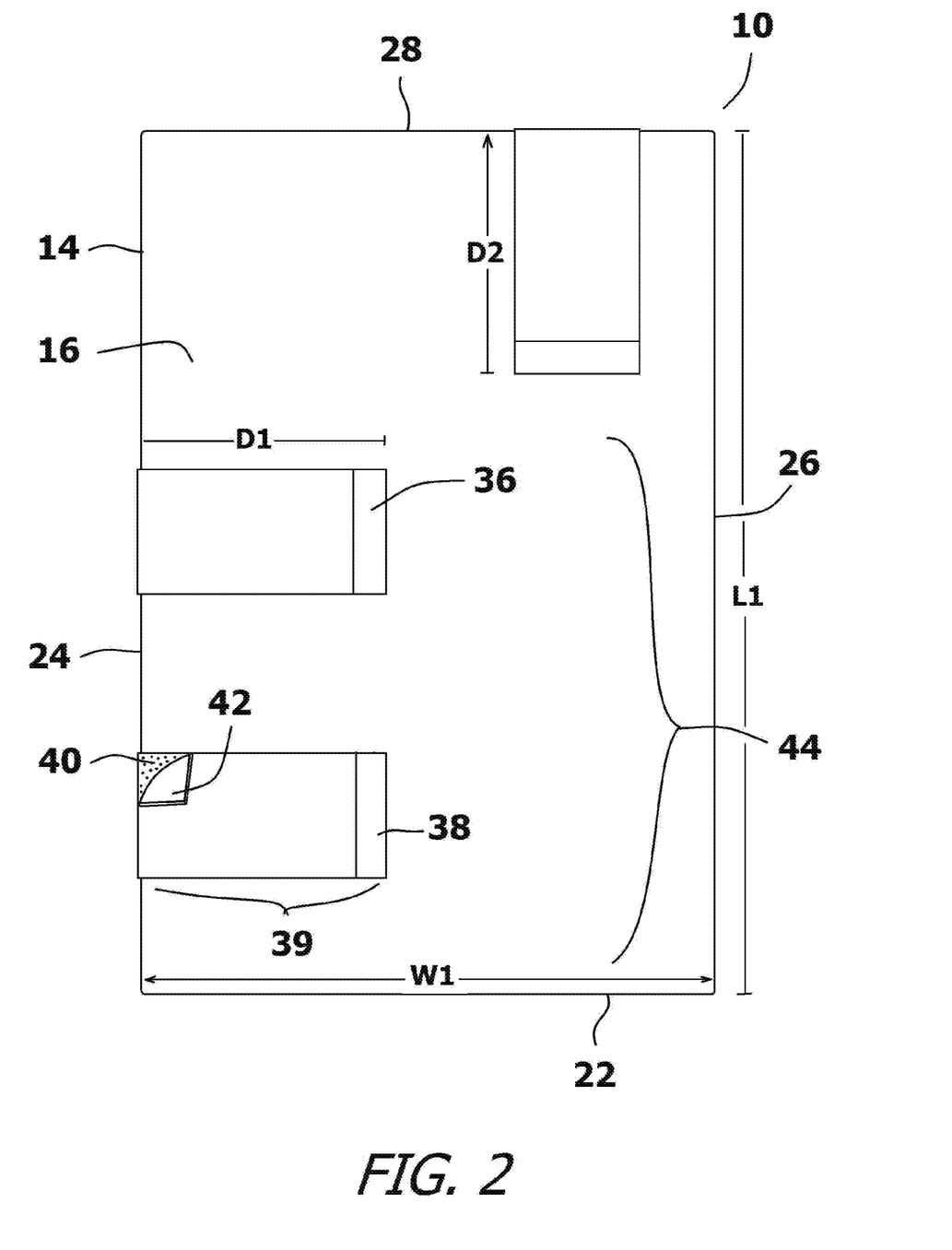
FIG. 2 is a front view of the embodiment of the isolation bag assembly shown in FIG. 1.
Figure 3:
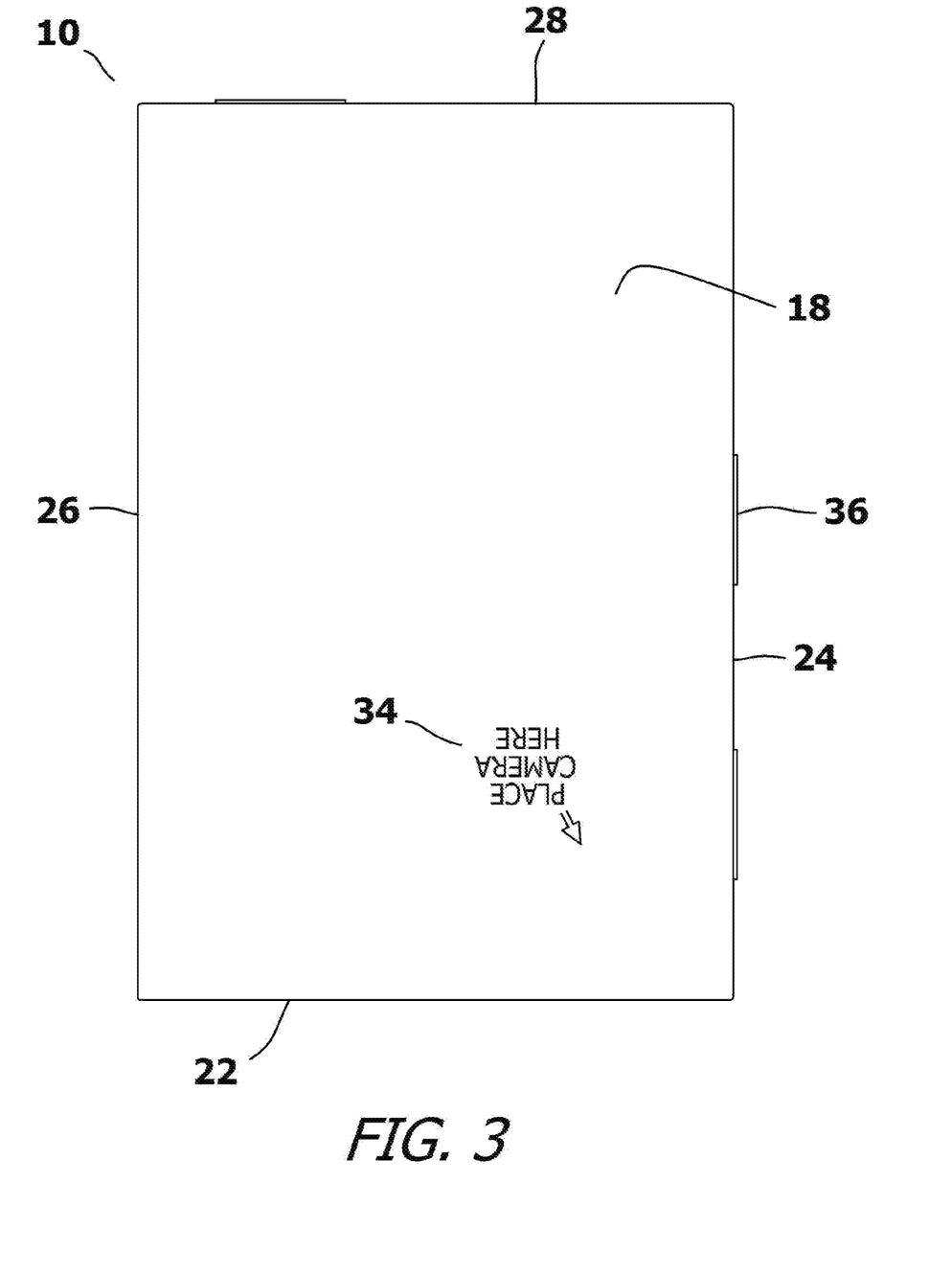
FIG. 3 is a rear view of the embodiment of the isolation bag assembly shown in FIG. 1 and FIG. 2.

Referring in combination to FIG. 1, FIG. 2, and FIG. 3, an isolation bag assembly 10 is shown in conjunction with a handheld electronic device 11. In the shown illustrations, the handheld electronic device 11 is a smartphone 12. However, it will be understood that the handheld electronic device 11 can be a tablet computer, a digital voice recorder, a digital music player, a remote-control handset, or the like. The purpose of the isolation bag assembly 10 is to isolate the handheld electronic device 11 so that it can be introduced into a clean environment, such as an operating room, without causing any contamination issues. The isolation bag assembly 10 also enables the handheld electronic device 11 to be viewed, heard, and otherwise operated, while remaining environmentally isolated.

The isolation bag assembly 10 includes a bag structure 14 made from a flexible sheet of a clear plastic. In this manner, the bag structure 14 can be easily folded and the contents of the bag structure 14 can be seen through the material of the bag structure 14. The bag structure 14 has a front panel 16 and an opposite rear panel 18 that are joined together along a bottom edge 22, a first side edge 24, and a second side edge 26. This provides the bag structure 14 with a first length L1 and a first width W1. The front panel 16 and the rear panel 18 are separated along a top edge 28, which is opposite the closed bottom edge 22. This creates an access opening 20 along the top edge 28 that leads into an interior 30 of the bag structure 14. The volume of the interior 30 is sufficient to accommodate most modern smartphones and similar handheld electronic devices.

Optional pull tabs 32 are provided on the front panel 16 and the rear panel 18 of the bag structure 14 proximate the top edge 28. The pull tabs 32 can be integrally formed as folded parts of the front panel 16 and the rear panel 18. Otherwise, the pull tabs 32 can be affixed to the front panel 16 and the rear panel 18. The pull tabs 32 enable a person to easily separate the front panel 16 and the rear panel 18 at the top edge 28, therein spreading the access opening 20 and enabling access to the interior 30 of the bag structure 14.

An orientation indicator 34 is printed on the rear panel 18 of the bag structure 14. The orientation indicator 34 assists a person in properly placing a handheld electronic device 11 in a clear area 44 within the bag structure 14. The clear area 44 is an area of the bag structure 14 where the front panel 16 and the rear panel 18 are unencumbered with any secondary structures. In the shown embodiment, the orientation indicator 34 states "camera here". This enables a person to properly orient a smartphone or a tablet with a camera when inserting that handheld electronic device 11 into the bag structure 14. It will be understood that such wording is exemplary, and that other wording and/or graphics can be used, depending upon the type of handheld electronic device 11 being used. A plurality of adhesive tabs 36 are provided on the front panel 16 of the bag structure 14. Each adhesive tab 36 has a base 38 that is adhered to the bag structure 14. Each base 38 is affixed to the front panel 16 at a first distance D1 from the first side edge 24. This first distance D1 corresponds with the edge of the clear area 44 of the bag structure 14. The first distance D1 is preferably between 10% and 33% of the first width W1 of the overall bag structure 14.

Each adhesive tab 36 also has a free section 39 that extends from the base 38. A layer of adhesive 40 is applied to the free section 39. The adhesive 40 is covered by a peel-way protective cover 42. In the shown embodiment two adhesive tabs 36 face the first side edge 24 of the bag structure 14. In addition, one adhesive tab 36 faces the top edge 28 of the bag structure 14. The adhesive tab 36 facing the top edge 28 has a base 38 that is a second distance D2 from the top edge 28. This second distance D2 is between 10% and 40% of the first length L1 of the overall bag structure 14. It will be understood that the numbers of adhesive tabs 36 illustrated is exemplary, and that any plurality of adhesive tabs 36 can be used.

The adhesive tabs 36 have bases 38 that are positioned a first distance D1 from the first side edge 24 and a second distance D2 from the top edge 28. This leaves the clear area 44 free of adhesive tabs 36. The clear area 44 is therefore defined between the adhesive tabs 36, the second side edge 26 and the bottom edge 22 of the bag structure 14. This clear area 44 is large enough to cover the handheld electronic device 11. As a result, when the handheld electronic device 11 is placed into the bag structure 14, the handheld electronic device 11 can be positioned under the clear area 44.

In the shown embodiment, the handheld electronic device 11 is a smartphone 12. The smartphone 12 has a touch screen 45 on a face surface and a camera 47 on a rear surface. The smartphone 12 is advanced into the bag structure 14 using the printed orientation indicator 34 as a guide. When properly positioned, the clear area 44 of the bag structure 14 will be positioned over both the touch screen 45 and the camera 47 of the smartphone 12.

Figure 4:
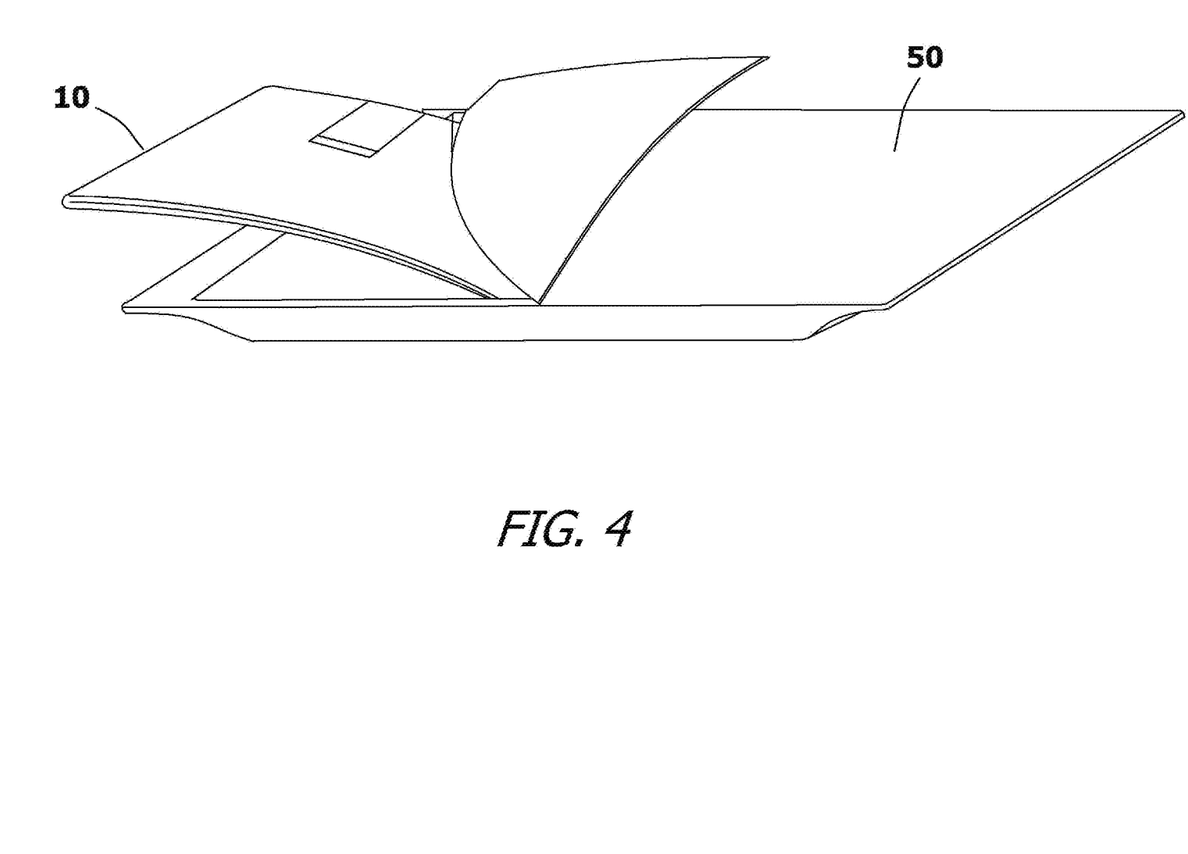
FIG. 4 shows the isolation bag assembly being removed from sterile packaging.

Referring to FIG. 4, in conjunction with FIG. 1, it will be understood that the isolation bag assembly 10 is sold prepackaged in medical grade sterile packaging 50. That is, the isolation bag assembly 10 is sterilized during manufacture. In a sterile packing environment, the sterilized isolation bag assembly 10 is sealed within sterile packaging 50. As a result, the isolation bag assembly 10 will remain sterile until the sterile packaging 50 is opened by a user.

Figure 5:
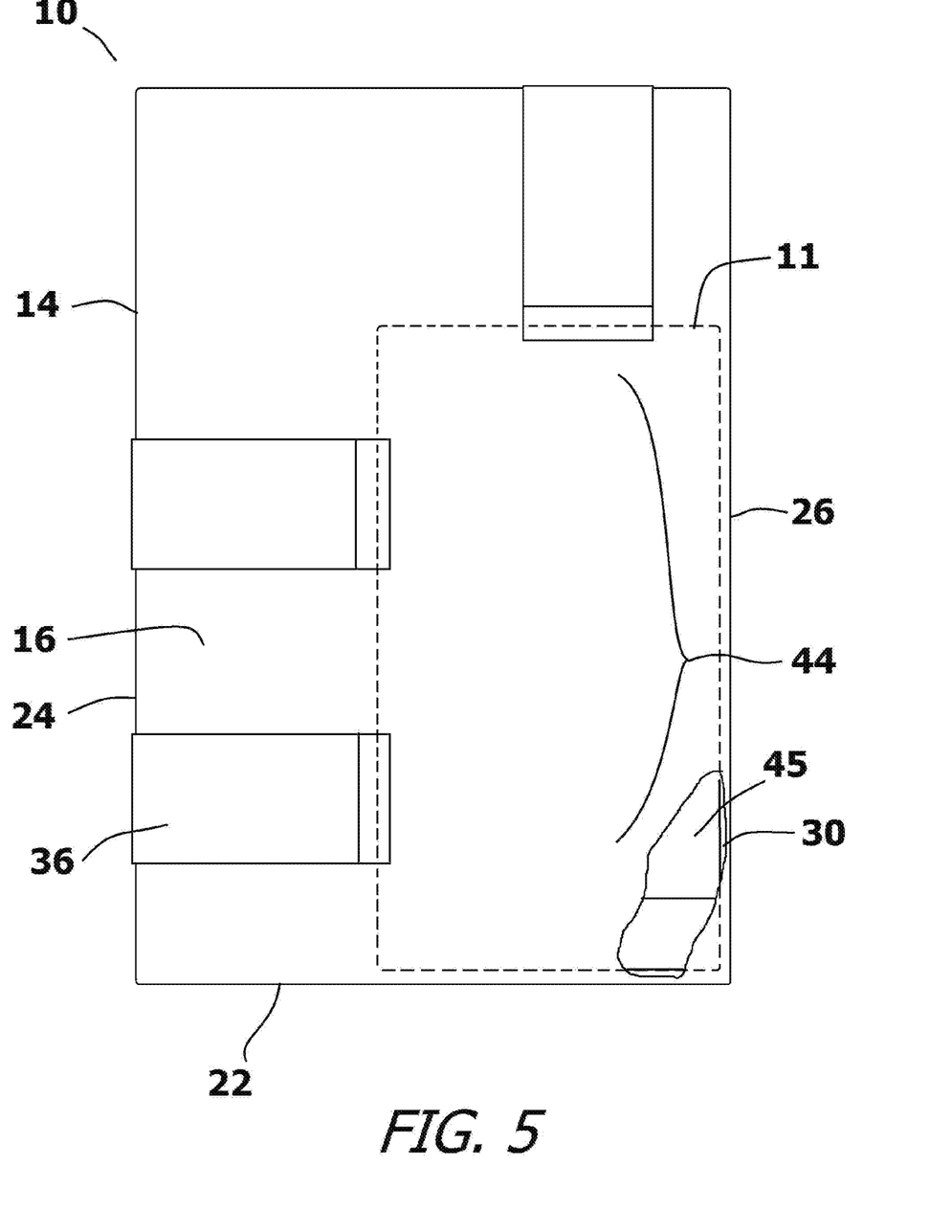
FIG. 5 shows the exemplary embodiment of FIG. 1 with the handheld electronic device inserted into the isolation bag assembly.

Referring to FIG. 5 in conjunction with FIG. 1, FIG. 2 and FIG. 3, it can be seen that once the isolation bag assembly 10 is removed from its sterile packaging 50, the handheld electronic device 11 is placed into the isolation bag assembly 10. The isolation bag assembly 10 is opened by an assistant who has not been uncontaminated. The isolation bag assembly 10 is removed from the opened sterile packaging 50 by a person in the clean room who has been decontaminated. The decontaminated person then opens the isolation bag assembly 10 using the pull tabs 32. The assistant then drops the handheld electronic device 11 into the isolation bag assembly 10 taking care not to contact the decontaminated person or anything on the exterior of the isolation bag assembly 10. The decontaminated person then closes the bag, therein isolating the handheld electronic device 11 within the bag.

Figure 6:
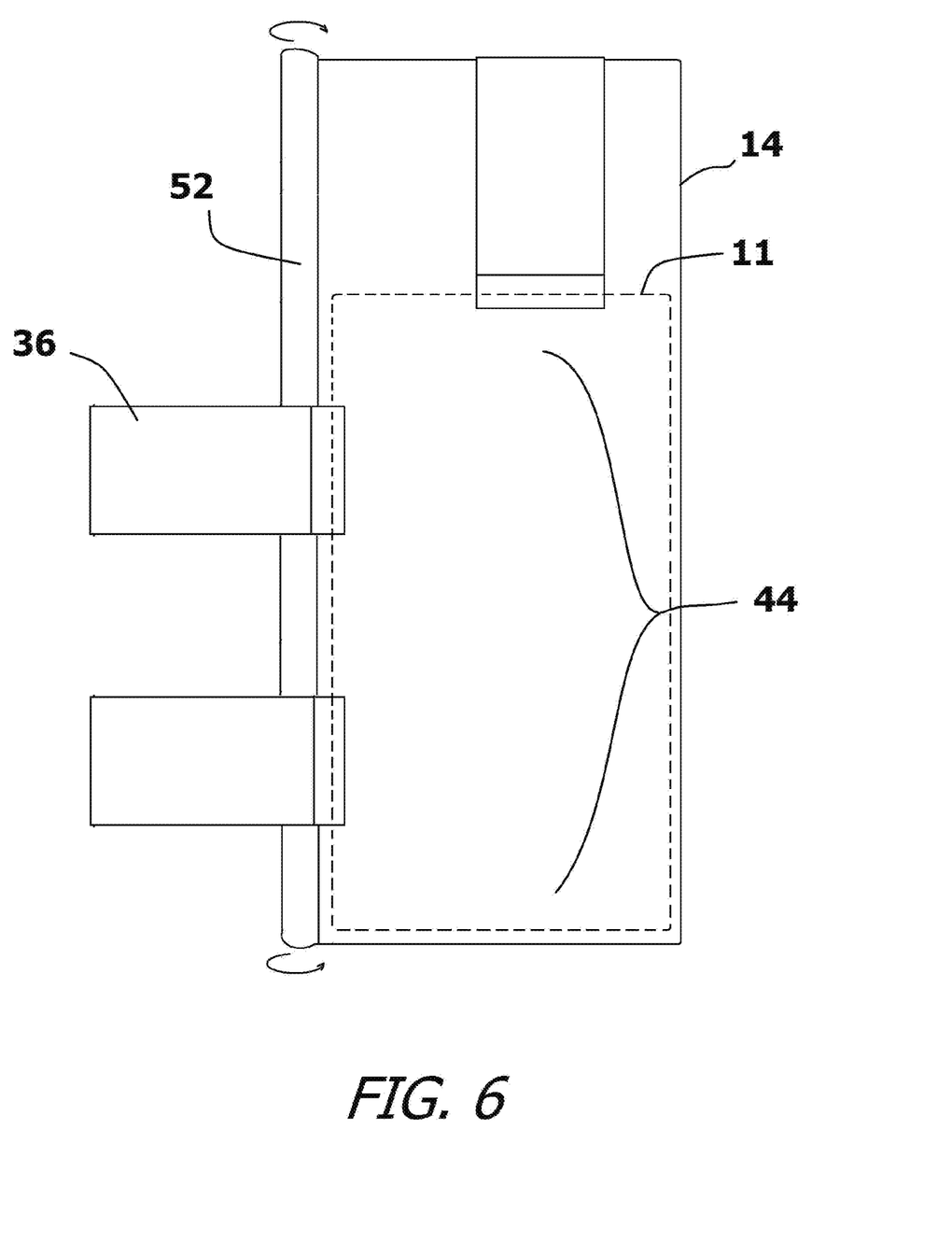
FIG. 6 shows the embodiment of FIG. 5 with a first edge of the isolation bag assembly folded and adhered.

Referring to FIG. 6, in conjunction with FIG. 1, FIG. 2 and FIG. 3, it can be seen that once the handheld electronic device 11 is placed in the isolation bag assembly 10, the first side edge 24 is rolled and/or folded toward the handheld electronic device 11. As the fold 52 reaches the handheld electronic device 11, the plastic of the bag structure 14 is made taut in the clear area 44 over the handheld electronic device 11. Once the fold 52 is at the handheld electronic device 11, the fold 52 is held in place by use of the adhesive tabs 36. The peel-away protective covers 42 are removed and the adhesive tabs 36 are pulled over the fold 52 to adhere the fold 52 in place.

Figure 7:
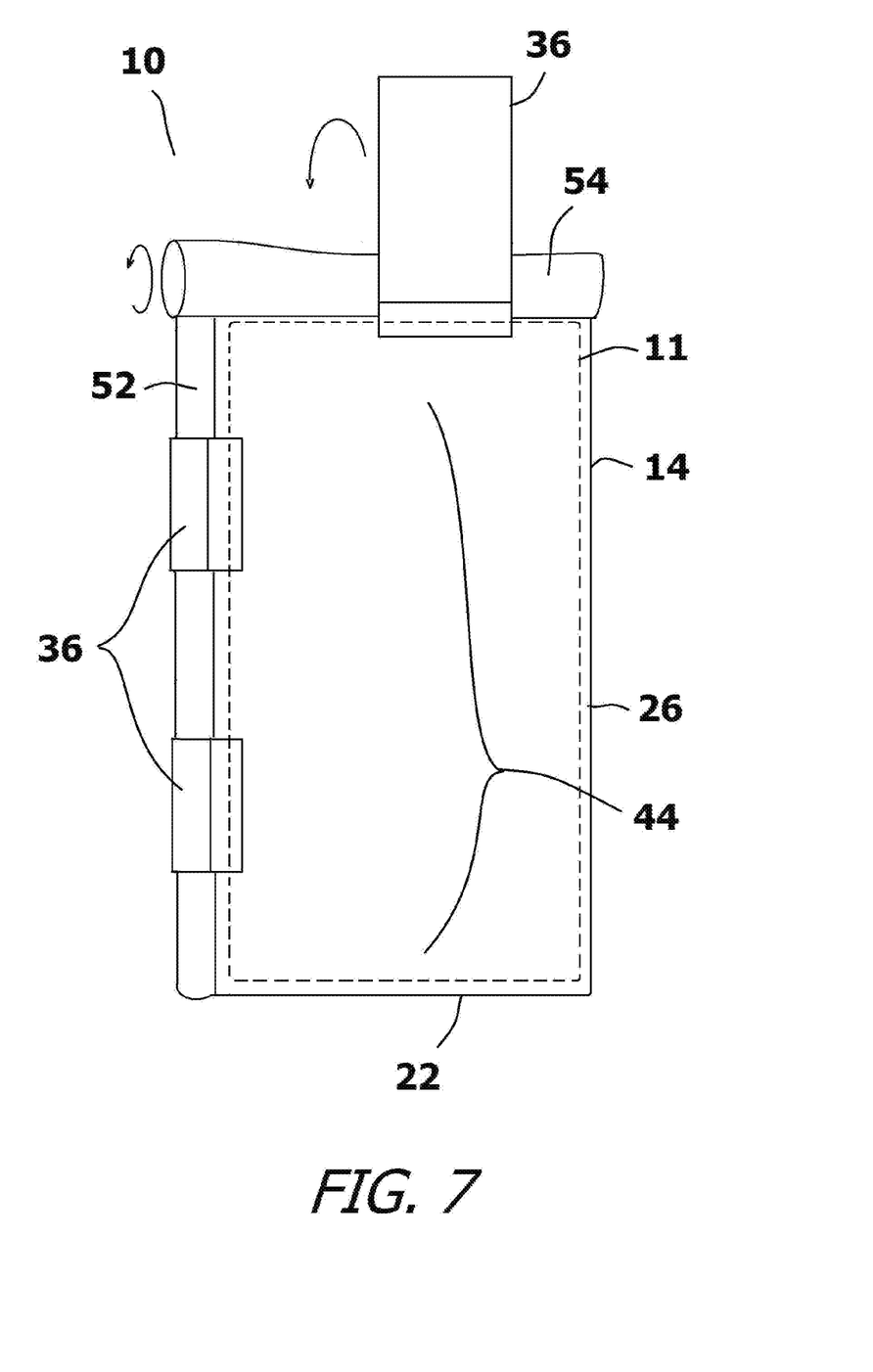
FIG. 7 shows the embodiment of FIG. 6 with a second edge of the isolation bag assembly folded and adhered.

Referring to FIG. 7, in conjunction with FIG. 1, FIG. 2, FIG. 3, and FIG. 6, it can be seen that the first side edge 24 is folded and closed with some adhesive tabs 36. The top edge 28 is then folded up to the handheld electronic device 11 and the resulting fold 54 is set with the remaining adhesive tab 36. At this point, the handheld electronic device 11 is encapsulated within the isolation bag assembly 10. The encapsulated handheld electronic device 11 can then be picked up and used by a decontaminated person without fear of cross-contamination.

The thin plastic material used to form the isolation bag assembly 10 enables the decontaminated person to utilize the touch screen 45 of the handheld electronic device 11, should it have such a screen. Likewise, any sound transmitted through the handheld electronic device 11 can be readily heard. Lastly, should the handheld electronic device 11 have a camera, such as with a smartphone, then the camera can image through the taut thin clear plastic. As such, clear pictures can be taken and viewed within the clean environment. The folds 52, 54 cause the bag structure 14 to reduce in size to match the exact size of the handheld electronic device 11. This keeps the handheld electronic device 11 in one fixed position relative the bag structure 14. It also keeps the bag structure 14 taut around the handheld electronic device 11. As such, there is no significant difference between handling the isolation bag assembly 10 or handling the handheld electronic device 11 itself. This makes the handheld electronic device 11 in the isolation bag assembly 10 easy to grasp and easy to operate. Furthermore, the derogations to picture and sound quality are minimal due to the taut nature of the bag structure 14.

It will be understood that the embodiment of the present invention that is illustrated and described is merely exemplary and that a person skilled in the art can make many variations to that embodiment. For instance, the size, shape and model of the bag structure can be changed to accommodate different electronic devices. All such embodiments are intended to be included within the scope of the present invention as defined by the claims.

What is claimed is:

1. An isolation bag assembly, comprising:
    a sterilized bag structure made from a flexible clear plastic and having a first length and a first width, wherein said sterilized bag structure has a front panel, a rear panel, a closed bottom, an open top, a first side edge, and a second side edge, wherein said front panel and said rear panel are joined along said closed bottom, said first side edge and said second side edge, wherein said first side edge and said second side edge have said first length and said closed bottom extends for said first width;
    a plurality of adhesive tabs affixed to said front panel of said sterilized bag structure, wherein each of said adhesive tabs has a base section that is affixed to said front panel at a first distance from said first side edge and a free section that extends from said base section toward said first side edge, wherein said first distance is between 10% and 33% of said first width, and wherein said free section has a layer of adhesive applied thereto that enables each said free section to selectively adhere to said sterilized bag structure when brought into contact with said sterilized bag structure.

2. The assembly according to claim 1, further including a peel-away protective cover for covering each said layer of adhesive.

3. The assembly according to claim 1, wherein each of said plurality of adhesive tabs has a second length, wherein said second length is at least as long as said first distance.

4. The assembly according to claim 1, further including at least one additional adhesive tab affixed to said front panel a first distance from said open top, wherein said at least one additional adhesive tab extends toward said open top.

5. The assembly according to claim 4, wherein said first distance is between 10% and 40% of said first length.

6. The assembly according to claim 1, further including pull tabs that extend from said front panel and said rear panel proximate said open top.

7. The assembly according to claim 1, further including sterilized packaging that surrounds said sterilized bag structure.

8. An isolation bag assembly, comprising:
    a sterilized bag structure made from a flexible clear plastic and having a first length and a first width, wherein said sterilized bag structure has a front panel, a rear panel, a closed bottom, an open top, a first side edge, and a second side edge, wherein said front panel and said rear panel are joined along said closed bottom, said first side edge and said second side edge, wherein said first side edge and said second side edge have said first length and said closed bottom extends for said first width;
    a first adhesive tab having a first base attached to said front panel a first distance said first side edge, wherein said first adhesive tab has a first free section that extends from said base toward said first side edge;
    a second adhesive tab having a second base attached to said front panel a second distance said open top, wherein said second adhesive tab has a second free section that extends from said base toward said open top;
    a mobile phone placed in an area within said bag structure, wherein said first side edge is folded to said area and is held in place by said first adhesive tab that is extended from said front panel to said rear panel, and wherein said open top is folded up to said area and is held in place with said second adhesive tab that is extended from said front panel to said rear panel.

9. The assembly according to claim 8, further including pull tabs that extend from said front panel and said rear panel proximate said open top.

* * * * *